United States Patent [19]

Székely et al.

[11] Patent Number: 4,565,827
[45] Date of Patent: Jan. 21, 1986

[54] 7-SUBSTITUTED PGI₂-DERIVATIVES AND PHARMACEUTICAL COMPOSITIONS CONTAINING THEM

[75] Inventors: István Székely, Dunakeszi; Marianna Lovász née Gáspár, Budapest; Gábor Kovács, Budapest; Krisztina Kékesi, Debrecen; Sándor Botár, Budapest; Károly Horváth, Budapest; Péter Körmöczy, Budapest; Pál Hadházy, Budapest; István Rákóczy, Budapest; László Fésüs, Debrecen, all of Hungary

[73] Assignee: CHINOIN Gyogyszer es Vegyeszeti Termekek Gyara R.T., Budapest, Hungary

[21] Appl. No.: 315,408

[22] Filed: Oct. 27, 1981

[30] Foreign Application Priority Data

Oct. 27, 1980 [HU] Hungary .................... 2587/80
Oct. 27, 1980 [HU] Hungary .................... 2588/80
Oct. 27, 1980 [HU] Hungary .................... 2589/80

[51] Int. Cl.⁴ ............... C07D 307/935; A61K 31/34; A61K 31/557
[52] U.S. Cl. .................... 514/469; 549/214; 549/465
[58] Field of Search ............ 549/465, 214; 542/426; 424/285; 514/469

[56] References Cited

PUBLICATIONS

Bannai et al., Tetrahedron Letters, vol. 22 (15), pp. 1417–1420 (Mar. 1981).
Fried et al., J. Med. Chem. (1980), vol. 23, pp. 234–237.

Primary Examiner—Henry R. Jiles
Assistant Examiner—Bernard I. Dentz
Attorney, Agent, or Firm—Karl F. Ross; Herbert Dubno

[57] ABSTRACT

The invention relates to new, 7-substituted PGI₂-derivatives of formula (I)

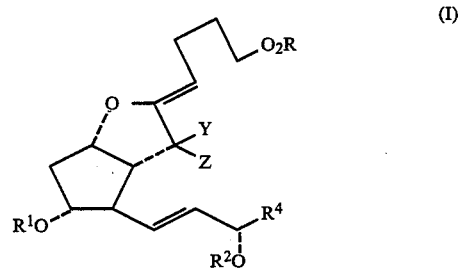

The new compounds have valuable therapeutical properties, and in particular show prostacyclin-like effects.

11 Claims, No Drawings

7-SUBSTITUTED PGI$_2$-DERIVATIVES AND PHARMACEUTICAL COMPOSITIONS CONTAINING THEM

The present invention relates to new, 7-substituted PGI$_2$-derivatives of formula (I)

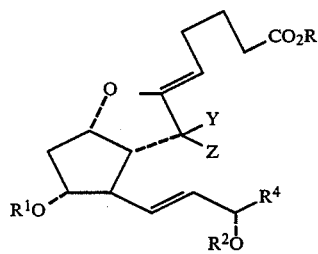

and to processes for the preparation thereof.

The substituents in formula (I) have the following meanings:

R is hydrogen, an alkali metal cation, a cation that can be derived from a pharmaceutically acceptable amine or an alkyl group of from one to four carbon atoms, R$^1$ and R$^2$ are hydrogen, a straight or branched alkanoyl of from one to four carbon atoms, benzoyl, tetrahydropyranyl, ethoxyethyl or trialkylsilyl containing alkyl groups of from one to four carbon atoms, R$^4$ is straight or branched alkyl of from three to seven carbon atoms or a substituted aryloxy group, Y is hydrogen, Z is fluoro, chloro or bromo or a group of formula —OR$^5$, wherein R$^5$ is hydrogen, straight or branched alkyl of from one to four carbon atoms, open-chain or cyclic acetal group, straight or branched alkanoyl of from one to four carbon atoms, benzoyl or trialkylsilyl containing alkyl groups of from one to four carbon atoms, or Y and Z together form a =N—OH, =N—OCH$_3$, =N—NH—CO—NH$_2$ or =N—N(CH$_3$)$_2$ group.

The new compounds of formula (I) can be manufactured according to our invention starting from the compounds of formula (II)

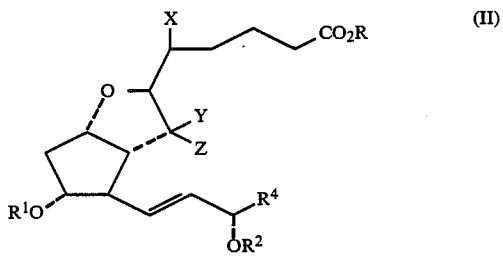

wherein R, R$^1$, R$^2$, R$^4$, Y and Z are as defined in formula (I), X is chloro, bromo or iodo, phenylselenyl or phenylthio group, via an elimination reaction; or starting from a compound of formulae (I) or (II) containing an oxo group in place of the Y and Z groups, and reacting this starting material with a corresponding oxoreagent, e.g. hydroxylamine or semicarbazine.

Where X is chloro, bromo or iodo, the elimination reaction is carried out in the presence of a base. As a base there can be used e.g. sodium carbonate, sodium hydroxide, sodium methylate, potassium t-butylate, 1,5-diazabicyclo(3.4.0)non-5-ene (DBN), 1,5-diazabicyclo(5.4.0)undec-5-ene (DBU), triethylamine or pyridine. The elimination reaction can also be carried out in a methylene chloride solution under stirring for some hours.

As a reaction medium there can be used water, alcohols, aromatic solvents (toluene, benzene), solvents containing an etheral bond (e.g. tetrahydrofurane, ethyleneglycol, dimethyl ether). In case DBN, DBU, triethylamine or pyridine is used as a base, there is no need for applying a solvent in addition thereto.

If X is phenylselenyl or phenylthio, the elimination reaction can be performed after transformation into selenium oxide with hydrogen peroxide, or after transformation into a sulfoxide with sodium methaperiodate [JACS, 95 2697, 6137 (1973), JACS, 82, 1810 (1960)].

Compounds of formula (I), wherein Z and Y form an =N—OH, =N—OCH$_3$, =N—NH—CO—NH$_2$ or =N—N(CH$_3$)$_2$ group, can be manufactured by reacting the corresponding oxo derivative, wherein Y and Z in formula (I) together form an oxo group, or a compound of formula (II), wherein Y and Z are oxo, with the corresponding hydroxyl amine derivative, with semicarbazide or with hydrazine in the presence of a tertiary amine. If a compound of formula (II) is used, also the elimination reaction takes place under the influence of the tertiary amine. In the above reactions preferably an acid addition salt of the oxo reagent is applied.

Starting compounds of formula (II) can be prepared by the following reactions.

PGF$_{2\alpha}$-derivatives esterified on the carboxylic groups and containing optionally protected hydroxyl groups at the 11- and 15-positions are reacted with a reagent hydroxylating in the allyl position, preferably with selenium dioxide. 4-hydroxy- and 7-hydroxy-PGF$_2$-derivatives are obtained as end-products; they can be separated from each other e.g. by chromatography, then the isolated 7-hydroxy-derivative is treated with an electrophylic reagent, e.g. with N-bromosuccinic imide or with phenylselenyl chloride. As an end-product, a compound of formula (II), wherein Y is hydrogen and Z is hydroxy, is obtained. 7-hydroxyl group of the obtained compounds can be halogenated, substituted, or transformed into an oxo group by a corresponding oxidizing agent, e.g. by pyridinium chlorochromate.

Alkyl group substituents having from one to four carbon atoms may be methyl, ethyl, n-propyl, isopropyl, n-butyl, isobutyl, sec-butyl or tert-butyl groups.

Alkyl group substituents having from three to seven carbon atoms may be straight or branched propyl, butyl, pentyl, hexyl or heptyl groups.

Alkanoyl group substituents having from one to four carbon atoms may be formyl, acetyl, propionyl or butiryl groups.

Cations that can be derived from a pharmaceutically acceptable amine may be those ammonium cations, which do not exhibit a toxic sideeffect in the application doses of compounds of formula (I). Such cations are e.g. various mono-, di- and tri-(C$_{1-4}$ alkyl)-ammonium cations, but substituted derivatives of these cations, e.g. with hydroxyl groups, are also applicable. Such a cation is e.g. the tris(hydroxymethyl)ammonium cation.

The aryloxy groups may be homocyclic or heterocyclic, the latter ones may contain from one to three heteroatoms, which may be identical or different. Such heteroatoms are nitrogen, sulfur or oxygen. Homocyclic aryloxy groups are e.g. phenoxy and naphthyloxy groups, while the most simple representative of the heterocyclic aryloxy groups is the pyridyloxy group. The aryloxy groups mentioned above may be unsubstituted or substituted. The preferable substituents are the halogen atoms, alkoxy groups containing from one to four carbon atoms in the alkyl part, the nitro group, the hydroxyl group or hydroxyl groups acylated with an alkanoyl group having from one to four carbon atoms.

If it is not stated otherwise, halogen atoms may be fluoro, chloro, bromo or iodo atoms. The trifluoromethyl group and the cyano group are also considered as members of the halogen atom group, though they only in some respects behave similarly to halogen atoms.

Novel compounds of formula (I) show a prostacyclin-like therapeutical effect. They inhibit blood platelet aggregation, promote loosening of the existing thrombus, decrease gastric acid secretion, show a cytoprotective effect of the liver and the stomach, dilate the coronary artery and the peripheral veins, inhibit formation of metastases. Due to their above effects they can be applied for therapeutical purposes.

The effect of the compounds according to the invention is given compared with the known prostacyclin sodium salt ($PGI_2$ sodium salt) as a standard. Antiaggregation activity was measured on blood plateletrich plasma isolated from rabbit blood, with the method of Born [Born, G. V. R.: Aggregation of blood platelets by adenosine diphosphate and its reversal, Nature, 194, 927 (1962)].

| Test compound | Relative effectiveness |
|---|---|
| $PGI_2$ | 1 |
| 7-oxo-$PGI_2$ | 1/15 |
| 7-hydroxy-$PGI_2$ (Z) | 1/40 |
| 7-hydroxy-$PGI_2$ (E) | 1/50 |
| 7-chloro-$PGI_2$ | 1/100 |
| 7-oxo-$PGI_2$—semicarbazide | 1/500 |

The $PGI_2$-analogues according to the invention are more advantageous than the prestacyclin because of their stability; they hydrolyze slowly in water, and therefore also their aqueous solutions can be used for pharmacological and for therapeutical purposes, too.

Some of the compounds according to the invention show advantageous properties also when compared with the 7-oxo-$PGI_2$ sodium salt of very high biological activity and stability. These advantages manifest themselves particularly in special fields of the antiaggregatory activity, e.g. in platelet aggregation caused by A-23187 $Ca^{2+}$ inophor, or in inhibition of the retention of platelets on glass beads. So it becomes possible to solve such therapeutical tasks which could not be solved with the known prostacyclin and 7-oxo-prostacyclin till now.

The pharmaceutical preparations may contain in addition to the active ingredients of formula (I) auxiliaries and fillers generally used in preparing medicaments. The preparations can be in solid form (e.g. tablets, dragées, capsules, powders etc.), in liquid form (e.g. injections and infusion solutions, drops, fluid medicines), or in semi-liquid form (e.g. creams, jellies etc.).

The preparations are preferably formulated in a unit dosage form, so their active ingredient content is identical with the dose to be taken or it is a part or a manifold of the dose. The daily dose for an adult is usually 0.1–1000 mg./kg., but it depends strongly on the severity of the disease, on tolerance of the patient and on the form of addition. The necessary amount of the active ingredient can easily be determined by the competent physician. It is very advantageous, that the novel active ingredients have a much more prolonged effect in the organism then that of the natural prostacyclins so the medicament need not be added to the patient so often.

Preparation of the compounds of formula (II) used as starting material in the process according to the invention is illustrated hereinbelow. Compounds of formula (I) wherein Y and Z are oxo, (7-oxo-$PGI_2$-derivatives) are disclosed in our European patent application published on July 8, 1981 under the No. 0 031 426.

PREPARATION 1

7-Hydroxy-$PGF_{2\alpha}$-methylester 507.5 mg. (1.4 mM) of $PGF_{2\alpha}$-methylester were dissolved in 5 ml of dry dioxane. The solution was heated on a 100° C. bath, then 311 mg. (2.8 mM) of selenium dioxide were added thereto and the obtained suspension was stirred for an hour. The reaction mixture was cooled and after adding 5 ml of 2.5% sodium bicarbonate, the solution was stirred for half an hour, then was extracted six times with 20 ml. portions of ethyl acetate. The organic layers were combined and dried over magnesium sulfate, filtered and evaporated. The crude product was chromatographed on a silica gel column with a 1:4 mixture of acetone and ethylacetate.

The fractions showing an $R_f$ value of 0.42 by thin layer chromatography using the mixture of acetone and ethyl acetate as eluent were collected. These fractions contained the 7-hydroxy-$PGF_{2\alpha}$-methylester. (Weight: 250 mg. (46.7%).

Fractions showing an $R_f$ value of 0.31 in the above analytical system were also collected. These fractions contained the 4-hydroxy-$PGF_{2\alpha}$-methylester. Weight after evaporation: 166.3 mg. (30.9%). Analysis data:

TLC on Merck silica gel G layer, with a 20:20:1 mixture of benzene:dioxane:acetic acid as eluent, $R_f$=0.495 and 0.485, respectively. With a 1:4 mixture of acetone and ethyl acetate as eluent, $R_f$=0.42 and 0.3, respectively.

NMR spectrum ($CDCl_3$) δ: 5.45–5.7 (m, 4H, olefinic protons), 4.0–4.8 (m, 4H, C$\underline{H}$OH protons), 3.65 (s, 3H, C$\underline{H}_3$O).

PREPARATION 2

7-Hydroxy-11,15-diacetyl-$PGF_{2\alpha}$-methylester 6.18 g. (12 mM) of 11,15-diacetyl-$PFG_{2\alpha}$-methylester were dissolved in 50 ml of dry dioxane. 2.66 g. (24 mM) selenium dioxide were added to the solution, then the obtained suspension was kept on a 100°–101° C. bath for 20 minutes. The reaction mixture was cooled, and 20 ml of 5% aqueous sodium bicarbonate solution was added thereto and the obtained mixture was stirred for another 30 minutes. The mixture then was extracted six times with 30 ml. portions of ether, the etheral phases were dried over magnesium sulfate, filtered and evaporated. The obtained crude product was chromatographed on a silica gel column with a 1:1 mixture of benzene and ethyl acetate.

Fractions showing an $R_f$ value of 0.43 and 0.35, respectively in the 2:1 mixture of ethylacetate and benzene, were collected and evaporated.

Fractions showing the $R_f$ value of 0.43 contain 7-hydroxy-11,15-diacetyl-$PGF_{2\alpha}$-methylester (weight: 2.01 g., 30.1%).

Following the process of preparations 1 and 2 and using the $PGF_{2\alpha}$-analogues protected on the 9-, 11- and 15-position hydroxy groups as starting materials, the 7-protected-$PGF_{2\alpha}$-derivatives can be obtained. Following the above process there can be manufactured also the corresponding 7-hydroxy-derivatives starting from the proper homo- nor- or aryloxy-$PGF_{2\alpha}$-derivatives.

PREPARATION 3

7-Chloro-9,11,15-triacetyl-$PGF_{2\alpha}$-methylester 400 mg. (1.55 mM) of triphenyl phosphine were dissolved in 5 ml of anhydrous carbon tetrachloride distilled over phosphorus pentoxide. In the obtained solution there were dissolved 520 mg. (1.02 mM) of 7-hydroxy-9,11,15-triacetyl-$PGF_{2\alpha}$-methylester under stirring. The reaction mixture was kept at the reflux temperature for 4 hours, then cooled to room temperature, and diluted with 50 ml of ether. Then the precipitated triphenyl phosphine oxide was filtered off and the filtrate was evaporated. The obtained crude product was chromatographed with a 4:1 mixture of benzene and ethyl acetate.

Fractions showing an $R_f$ value of 0.68 in a 2:1 mixture of benzene and ethyl acetate as an eluent (chromatographed twice on analytical silica gel layer, Merck) were collected and evaporated. The obtained title product weights 232 mg. (44%). Analysis results:

TLC on Merck silica gel twice with a 20:20:1 mixture of benzene:dioxane:acetic acid, $R_f = 0.68$.

Following the above process all 7-hydroxy-$PGF_{2\alpha}$-derivatives can be transformed into the corresponding 7-chloro-derivatives, or, using the proper halogenating agent, into other 7-halogen-derivatives.

PREPARATION 4

5-Bromo-7-hydroxy-11,15-diacetyl-$PGI_1$-methylester 202 mg. (0.43 mM) of 7,9-hydroxy-11,15-diacetyl-$PGF_{2\alpha}$-methylester were dissolved in 6 ml. of the 1:1 mixture of anhydrous tetrahydrofuran and anhydrous chloroform. The solution was cooled to $-78°$ C., argon was passed through the flask over the liquid, then 84.2 mg. (0.47 mM) of solid N-bromosuccinic imide were added to the solution.

The acetone/dry-ice bath was removed and the reaction mixture was allowed to warm to room temperature, then it was stirred at room temperature for another 20 minutes. Then the reaction mixture was diluted with 30 ml of ether, the organic layer was washed with 5 ml of water, dried over magnesium sulfate, filtered and evaporated. Weight: 214 mg. (92%). The crude product gives three spots in the 1:1 mixture of benzene and ethyl acetate, at the $R_f$ values of 0.51, 0.6 and 0.69, since it is a mixture of the 6- and 7-epimers. The spots can be separated by column chromatography with a 3:1 mixture of benzene and ethylacetate, but the crude product can also directly be used in further reactions. Analysis results:

TLC on silica gel G layer with a 1:1 mixture of benzene and ethylacetate, $R_f = 0.51$, 0.6 and 0.69, respectively (developed with phosphomolybdic acid);

NMR spectrum data (CDCl$_3$) δ: 5.45–5.75 (m,2H, olefinic protons) 5.15 (q,1H, C$\underline{H}$OAc) 4.65–4.95 (m,2H, C$\underline{H}$OAc and C$\underline{H}$O) 4.0–4.35 (m,2H, C$\underline{H}$) 3.65 (s,3H, C$\underline{H}_3$O) 2.05–2.08 (s+s,3H+3H

In case the process of Preparation 4 is followed except that elementary iodine is used in place of N-bromosuccinic imide, the corresponding 5-iodo-derivatives are obtained. Replacing the N-bromosuccinic imide by phenylselenyl bromide, 5-phenylselenyl-derivatives are obtained.

PREPARATION 5

5-Bromo-7-(1-ethoxy-ethoxy)-11,15-diacetyl-$PGI_1$-methylester 413 mg (0.75 mM) of 5-bromo-7-hydroxy-11,15-acetyl-$PGI_1$-methylester were dissolved in 5 ml of dry dichloromethane, then 700 μl. (540 mg.) of ethylvinylether and one drop of 10% p-toluenesulfonic acid in tetrahydrofurane were added to the solution. The reaction mixture was stirred at room temperature for 30 minutes, then the p-toluenesulfonic acid catalyst was neutralized with a drop of triethyl amine. The reaction mixture was diluted with 30 ml of dichloromethane and washed with a 2.5% sodium bicarbonate solution. The organic layer was dried over magnesium sulfate, filtered and evaporated. The crude product was chromatographed with a 5:1 mixture of benzene and ethyl acetate.

Fractions showing $R_f$ values of 0.39 and 0.29, respectively, in a 4:1 mixture of benzene and ethyl acetate, are collected and evaporated. 279 mg. (60%) of an epimer mixture are obtained. Analysis results:

NMR (CDCl$_3$) δ: 5.5–5.8 (m,4H, olefinic protons) 5.1–5.4 (m, 1H, C$\underline{H}$OA) 4.5–5.0 (m,4H, C$\underline{H}$OAc+O$\underline{H}$OC) 4.0–4.4 (m,4H, C$\underline{H}$OC) 3.65 (s, 3H, $\overline{C}H_3$O) 3.5–3.8 (m, 3H, C$\underline{H}$Br+$\overline{O}$CH$_2$CH$_3$) 2.05 (s, 6H, CH$_3$CO) 0.95 (t, 3H, $\overline{C}$H$_2$C$\underline{H}_3$)

Following the processes of Preparations 1 to 5 all compounds of formula (II) necessary for realizing the process according to our invention can be manufactured.

It is not deemed necessary to illustrate the processes for conveying up or splitting off the protective groups, the esterification, saponification, or salt forming reactions, because they are quite obvious for a person skilled in the art.

The following examples illustrate the invention without restricting its scope.

EXAMPLE 1

7-Hydroxy-$PGI_2$-methylester 10 ml of 1,5-diazabicyclo(3.4.0)non-5-ene were added to 1.17 g. (2.45 mM) of 5-bromo-7-hydroxy-$PGI_1$-methylester under stirring, at room temperature. The reaction mixture was stirred for another 15 minutes, diluted 100 ml. ether, washed with three times with 5 ml of water, then with 10 ml of saturated salt solution, dried over magnesium sulfate, filtered and evaporated. The obtained crude product (weight 1.5 g.) was chromatographed on a silica gel column using a 3:1 mixture of benzene and ethyl acetate. 680.2 mg. (70.4%) of end-product were obtained. Analysis results:

TLC on Merck silica gel G layer with 3:1 mixture of ethyl acetate and triethyl amine, $R_f = 0.28$;

NMR spectrum (CDCl$_3$) δ: 5.65–5.8 (m, 1H) 5.4–5.65 (m, 2H) 4.3–4.6 (m, 1H) 3.9–4.2 (m, 3H) 3.68 (s, 3H).

EXAMPLE 2

7-(1-ethoxy-ethoxy)-11,15-diacetyl-PGI$_2$-methylester

The procedure described in example 1 was followed except that in place of 5-bromo-7-hydroxy-PGI$_1$-methylester 1.57 g. (2.54 mM) of 7-(1-ethoxy-ethoxy)-5-bromo-11,15-diacetyl-PGI$_1$-methylester were used.

942.7 mg. (68.9%) of end-product were obtained. Analysis results:

TLC on Merck silica gel G layer with a 3:1 mixture of benzene and ethyl acetate, $R_f$=0.25;

NMR spectrum(CDCl$_3$) δ: 5.45–5.9 (m, 3H) 5.05–5.2 (m, 1H) 4.5–5.0 (m, 2H) 4.0–4.25 (m, 2H) 3.66 (s, 3H) 3.4–4.6 (m, 2H).

EXAMPLE 3

7-Methoxy-11,15-diacetyl-PGI$_2$-methylester

The procedure described in example 1 was followed except that in place of 5-bromo-7-hydroxy-PGI$_1$-methylester 1.42 g. (2.54 mM) of 5-bromo-7-methoxy-11,15-diacetyl-PGI$_1$-methylester were used.

849.2 mg. (69.6%) of end-product were obtained. Analysis result:

TLC on Merck silica gel G layer with a 2:1 mixture of benzene and ethyl acetate, $R_f$=0.63.

EXAMPLE 4

7-Chloro-11,15-diacetyl-PGI$_2$-methylester

The procedure described in example 1 was followed, except that in place of 5-bromo-7-hydroxy-PGI$_1$-methylester 1.43 g. (2.54 mM) of 5-bromo-7-chloro-11,15-diacetyl-PGI$_1$-methylester were used. 864.7 mg. (70.2%) of end-product were obtained. Analysis result:

TLC on Merck silica gel G layer with a 2:1 mixture of benzene and ethyl acetate, $R_f$=0.66.

EXAMPLE 5

7-Keto-11,15-diacetyl-PGI$_2$-methylester-semicarbazone 70 mg. (0.15 mM) of 7-keto-11,15-diacetyl-PGI$_2$-methylester were dissolved in 5 ml of ethanol. To the solution there were added 15 μl. (0.18 mM) of pyridine, then dropwise a solution of 20 mg. (0.18 mM) of semicarbazide hydrochloride in 2 ml of water. The mixture was stirred at 60° C. for 3 hours, then cooled, diluted with 30 ml of ether and extracted with 10 ml of water. The etheral layer was dried over magnesium sulfate, filtered and evaporated.

The obtained crude product (weight 80.5 mg.) was chromatographed on a silica gel column, using a 4 to 1 mixture of benzene and ethyl acetate as eluent. The fractions are analysed by TLC (a 3:1 mixture of benzene and ethyl acetate was used as eluent, the spots were developed with phosphomolybdic acid). Fractions showing $R_f$ values of 0.28 and 0.34 were collected and evaporated; 43 mg. (55%) of end-product was obtained. Analysis:

TLC on Merck silica gel G layer with a 3 to 1 mixture of benzene and ethyl acetate, $R_f$=0.28 and 0.34.

EXAMPLES 6 TO 8

The procedure of example 5 was followed, except that in place of semicarbazide hydrochloride the reagents defined hereinbelow were used:

12.51 mg. (0.18 mM) of hydroxylamine hydrochloride; the end-product was 45.60 mg. (53%) of 7-keto-11,15-diacetyl-PGI$_2$-methylester-oxime; $R_f$=0.1 and 0.6;

14.51 mg. (0.18 mM) of O-methyl-hydroxylamine hydrochloride; the end-product was 46.62 mg. (52.8%) of 7-keto-11,15-diacetyl-PGI$_2$-methylester-O-methoxime;

17.38 mg. (0.18 mM) of N,N-dimethyl-hydrazine hydrochloride; the end-product was 49.33 mg. (54.2%) of 7-keto-11,15-diacetyl-PGI$_2$-methylester-N,N-dimethyl-hydrazone.

We claim:

1. A compound of the formula (I)

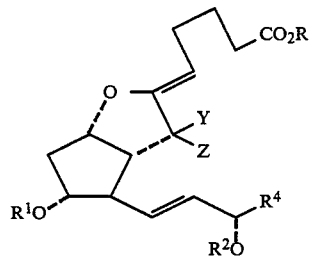

wherein

R is hydrogen, an alkali metal cation, a cation that is derived from a pharmaceutically acceptable amine, or an alkyl group having 1 to 4 carbon atoms;

$R^1$ and $R^2$ are hydrogen, a straight or branched alkanoyl of 1 to 4 carbon atoms, benzoyl, tetrahydropyranyl, ethoxyethyl or trialkylsilyl containing alkyl groups of 1 to 4 carbon atoms;

$R^4$ is straight or branched alkyl of 3 to 7 carbon atoms;

Y is hydrogen;

Z is fluoro, chloro, bromo or a group of the formula —$OR^5$, wherein $R^5$ is hydrogen, straight or branched chain alkyl of 1 to 4 carbon atoms, straight or branched alkanoyl of 1 to 4 carbon atoms, benzoyl, or trialkylsilyl containing alkyl groups of 1 to 4 carbon atoms, or Y and Z together form a =N—OH, =N—OCH$_3$, =N—NH—CO—NH$_2$ or =N—N(CH$_3$)$_2$ group.

2. A compound of the formula:

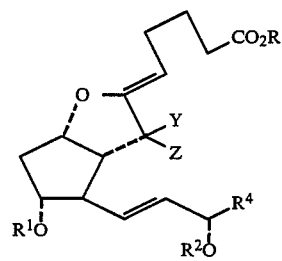

wherein

R is hydrogen, an alkali metal cation, a cation that is derived from a pharmaceutically acceptable amine, or an alkyl group having 1 to 4 carbon atoms;

$R^1$ and $R^2$ are hydrogen, straight or branched alkanoyl of 1 to 4 carbon atoms, benzoyl, tetrahydropyranyl, ethyoxyethyl or trialkylsilyl containing alkyl groups of 1 to 4 carbon atoms;

$R^4$ is straight or branched alkyl of 3 to 7 carbon atoms;

Y is hydrogen; and

Z is fluoro, chloro or bromo.

3. A compound of the formula

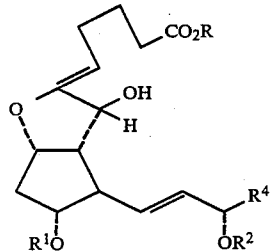

wherein

R is hydrogen, an alkali metal cation, a cation that is derived from a pharmaceutically acceptable amine or an alkyl group of from one to four carbon atoms, $R^1$ and $R^2$ are straight or branched alkanoyl of from one to four carbon atoms, benzoyl, tetrahydropyranyl, ethoxyethyl or trialkyl-silyl containing alkyl groups of from one to four carbon atoms and $R^4$ is straight or branched alkyl of from three to seven carbon atoms.

4. 7-Hydroxy-$PGI_2$-methylester.

5. 7-(1-ethoxy-ethoxy)-11,15-diacetyl-$PGI_2$-methylester.

6. 7-Methoxy-11,15-diacetyl-$PGI_2$-methylester.

7. 7-Chloro-11,15-diacetyl-$PGI_2$-methylester.

8. 7-Keto-11,15-diacetyl-$PGI_2$-methylester-semicarbazone.

9. A pharmaceutical composition having the ability to inhibit thrombocyte aggregation which comprises a pharmaceutically effective amount of the compound of the formula (I) as defined in claim 1 along with a pharmaceutically acceptable auxiliary or filler.

10. A method of inhibiting thrombocyte aggregation in an animal subject which comprises the step of administering to said animal subject a pharmaceutically effective amount of the compound of the formula (I) as defined in claim 1.

11. A compound of the formula:

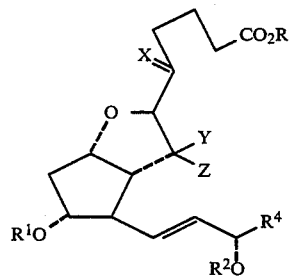

wherein

R is hydrogen, an alkali metal cation, a cation that is derived from a pharmaceutically acceptable amine or an alkyl group of from one to four carbon atoms, $R^1$ and $R^2$ are hydrogen, straight or branched alkanoyl of from one to four carbon atoms, benzoyl, tetrahydropyranyl, ethoxyethyl or trialkylsilyl containing alkyl groups of from one to four carbon atoms $R^4$ is straight or branched alkyl of from three to seven carbon atoms, X is chlorine, bromine or iodine Y is hydrogen and Z is fluoro, chloro or bromo.

* * * * *